United States Patent [19]

Unger et al.

[11] Patent Number: 5,714,528

[45] Date of Patent: *Feb. 3, 1998

[54] CONTRAST MEDIA FOR ULTRASONIC IMAGING

[75] Inventors: Evan C. Unger; Guanli Wu, both of Tucson, Ariz.

[73] Assignee: ImaRx Pharmaceutical Corp., Tucson, Ariz.

[*] Notice: The term of this patent shall not extend beyond the expiration date of Pat. No. 5,420,176.

[21] Appl. No.: 458,667

[22] Filed: Jun. 2, 1995

Related U.S. Application Data

[62] Division of Ser. No. 391,936, Feb. 21, 1995, Pat. No. 5,639,442, which is a division of Ser. No. 58,098, May 5, 1993, Pat. No. 5,420,176, which is a continuation of Ser. No. 708,731, May 31, 1991, abandoned, which is a continuation-in-part of Ser. No. 532,213, Jun. 1, 1990, abandoned.

[51] Int. Cl.$^6$ .............................. C08L 1/02; A61K 49/00
[52] U.S. Cl. ..................... 523/205; 523/212; 523/213; 523/200; 524/35; 524/837; 536/56; 514/57; 424/9.4; 424/9.5
[58] Field of Search .................... 424/9.5, 9.4; 514/57; 523/200, 205, 212, 213; 524/35, 837; 536/56

[56] References Cited

U.S. PATENT DOCUMENTS

| | | | |
|---|---|---|---|
| 2,925,365 | 2/1960 | Nicholson et al. | 106/203 |
| 2,934,472 | 4/1960 | May | 424/125 |
| 3,251,824 | 5/1966 | Battista | 106/203 |
| 4,028,172 | 6/1977 | Mazzarella | 162/164 |
| 4,101,647 | 7/1978 | Clauss et al. | 424/5 |
| 4,269,068 | 5/1981 | Molina | 73/644 |
| 4,337,095 | 6/1982 | Leoni et al. | 106/203 |
| 4,365,516 | 12/1982 | Molina | 73/644 |
| 4,390,692 | 6/1983 | Green | 563/84 |
| 4,518,727 | 5/1985 | Traver | 524/35 |
| 4,652,593 | 3/1987 | Kawahara et al. | 523/116 |
| 4,716,225 | 12/1987 | Ledley et al. | 536/122 |
| 4,735,659 | 4/1988 | Bishop | 106/193 |
| 4,744,987 | 5/1988 | Mehra et al. | 106/203 |
| 4,844,882 | 7/1989 | Widder et al. | 424/9 |
| 5,091,448 | 2/1992 | Hostettler et al. | 524/501 |
| 5,420,176 | 5/1995 | Unger et al. | 523/212 |

FOREIGN PATENT DOCUMENTS

| | | |
|---|---|---|
| 34872/78 | 4/1977 | Australia. |
| 54929/80 | 1/1979 | Australia. |
| 911629 | 10/1972 | Canada. |
| 1030186A | 1/1989 | China. |
| 1030186A | 11/1989 | China. |
| 77752 A3 | 4/1983 | European Pat. Off.. |
| 0212870 | 3/1987 | European Pat. Off.. |
| 2546066 | 11/1984 | France. |
| 2951319 | 7/1981 | Germany. |
| 32463863 | 6/1984 | Germany. |
| 45-18999 | 6/1970 | Japan. |
| 57-206611 | 12/1982 | Japan. |

OTHER PUBLICATIONS

Noll, *Chemistry and Technology of Silicones*, pp. 515–521 (Academic Press 1968).

Stark et al., *The Interactions between Trialkylsilanes and E–Glass or Aerosil Surfaces. Reactions of Trimethylsilanol, Trimethylchlorosilane, and Hexamethyldisilazane*, J. Phys. Chem., vol. 72, No. 8, pp. 2750–2754 (1968).

Warren et al., *The Liquid–Filled Stomach –An Ultrasonic Window To The Upper Abdomen*, JCU, vol. 6, pp. 315–320 (1978).

*The United States Pharmacopeia –The National Formulary*, 22nd Revision, Jan. 1, 1990, Mack Printing Company, Easton, PA.

Helzel, *Initial Experience with the Use of "Contrast Media" (so-called Sonographica) in Ultrasonic Examination of the Upper Abdomen*, Fortschr. Rontgenstr., vol. 140, No. 3, pp. 337–340 (1984) (German article and English language translation).

Chem. Abstracts, vol. 69, No. 61770x, p. 5786 (1968).
Chem. Abstracts, vol. 74, No. 54904u, pp. 51–52 (1971).
Chem. Abstracts, vol. 70, No. 116405k, p. 88 (1969).
Chem. Abstracts, vol. 75, No. 9271v, p. 220 (1971).
Indus. Organics, vol. 77, No. 37150q, p. 37160 (1972).
Hertl et al., J. Phys. Chem. vol. 75, No. 14, pp. 2181–2185 (1971).

Noll et al., *Chemistry and Technology of Silicones*, pp. 414–421 (Academin Press 1968).

Struve et al., *KrankenhausArzt*, vol. 58, No. 4, pp. 360–364 (1985) (both German language and English language translation).

Sommer et al., Radiology, vol. 125, No. 1, pp. 219–221 (1977).

*Primary Examiner*—Andrew E.C. Merriam
*Attorney, Agent, or Firm*—Woodcock Washburn Kurtz Mackiewicz & Norris LLP

[57] ABSTRACT

Novel contrast media for use in ultrasonic imaging are described. Such contrast media may be comprised of an aqueous solution of one or more biocompatible polymers, wherein said biocompatible polymers are coated with and/or in admixture with at least one silicon containing compound. Alternatively, the contrast media may be comprised of an aqueous solution of one or more biocompatible synthetic polymers, or an aqueous solution of cellulose. The contrast media maybe employed, if desired, with anti-gas agents and/or suspending agents.

22 Claims, 11 Drawing Sheets

CONTRAST MEDIA FOR ULTRASONIC IMAGING

CROSS-REFERENCE TO RELATED APPLICATIONS

This application is a divisional of U.S. Ser. No. 391,936, filed Feb. 21, 1995, now U.S. Pat. No. 5,639,442, which in turn is a divisional of U.S. Ser. No. 058,098, filed May 5, 1993, now U.S. Pat. No. 5,420,176, which in turn is a continuation of U.S. Ser. No. 708,731, filed on May 31, 1991, now abandoned, which in turn is a continuation-in-part application of U.S. Ser. No. 532,213, filed on Jun. 1, 1990, now abandoned.

BACKGROUND OF THE INVENTION

1. Field of the Invention

This invention relates to the field of ultrasonic imaging, and more specifically to the use of polymers as contrast agents for ultrasonic imaging.

2. Description of the Prior Art

There are a variety of imaging techniques that have been used to diagnose disease in humans. One of the first imaging techniques employed was X-rays. In X-rays, the images produced of the patient's body reflect the different densities of body structures. To improve the diagnostic utility of this imaging technique, contrast agents are employed in an attempt to increase the differences in density between various structures, such as between the gastrointestinal tract and its surrounding tissues. Barium and iodinated contrast material, for example, are used extensively for X-ray gastrointestinal studies to visualize the esophagus, stomach, intestines and rectum. Likewise, these contrast agents are used for X-ray computed tomographic studies to improve visualization of the gastrointestinal tract and to provide, for example, contrast between the tract and the structures adjacent to it, such as the vessels or the lymph nodes. Such gastrointestinal contrast agents permit one to increase the density inside the esophagus, stomach, intestines and rectum, and allow differentiation of the gastrointestinal system from surrounding structures.

Ultrasound is a more recent imaging technique which, unlike X-rays, does not utilize ionizing radiation. Instead, in ultrasound, sound waves are transmitted into a patient. These sound waves are then reflected from tissue in the patient and are received and processed to form an image. Since ultrasound does not employ ionizing radiation to produce these images, ultrasound is less invasive and safer to the patient than X-ray imaging techniques. Ultrasound, however, suffers at times in imaging clarity in comparison to X-rays, particularly where imaging of the gastrointestinal tract is involved. In ultrasound, one major problem is the presence of air/fluid interfaces, which results in shadowing of the ultrasound beam. Shadowing, in turn, prevents the ultrasound beam from penetrating beyond the air/fluid interface, and thus prevents visualization of structures near any air pockets. Another problem with ultrasound is the difficulty in imaging adjacent hypoechoic structures, that is, structures that are only minimally reflective of the ultrasound beam and, therefore, result in a low ultrasound signal. These problems are particularly evident in the gastrointestinal region, with its many air/liquid interfaces and its adjacent fluid-filled mucosal lining and often fluid-containing lumen. If better contrast agents were available for ultrasound, the diagnostic accuracy and the overall usefulness of ultrasound as an imaging modality, particularly in the gastrointestinal region, would be greatly enhanced.

In the past, investigators have attempted to solve the problems associated with gastrointestinal ultrasonic imaging by using water to fill the gastrointestinal tract. Water, however, was found to simply mix with the gas, and thus much of the shadowing resulting from the presence of air/fluid interfaces remained. In addition, the fact that water is absorbed by the bowel decreased its ability to serve any meaningful contrast enhancement function distally within the tract. Furthermore, the water is hypoechoic, and its presence adjacent to the fluid-filled hypoechoic mucosal lining of this region resulted in little differentiation of the tract lumen and from its lining. Intravenously administered glucagon has been employed in connection with such gastrointestinal imaging, since glucagon administered in this fashion relaxes the bowel by decreasing peristalsis. Although a helpful ultrasound adjunct, this, however, does not address such problems as shadowing caused by air/fluid interfaces and low differentiation caused by the presence of adjacent hypoechoic structures.

The need is great for contrast agents useful in ultrasonic imaging of various regions of the body, particularly those useful in imaging the gastrointestinal tract. The present invention is directed to these important ends.

SUMMARY OF THE INVENTION

The present invention is directed to a contrast medium useful for ultrasonic imaging.

Specifically, the invention pertains to a contrast medium comprising an aqueous solution of at least one biocompatible polymer, wherein said biocompatible polymer is coated with and/or in admixture with at least one silicon containing compound.

The invention also pertains to a contrast medium comprising an aqueous solution of at least one biocompatible synthetic polymer.

The invention further pertains to a contrast medium comprising an aqueous solution of cellulose.

Further, the subject invention encompasses a method of providing an image of an internal region of a patient, especially an image of the gastrointestinal region of the patient, said method comprising (i) administering to the patient one or more of the aforementioned contrast media, and (ii) scanning the patient using ultrasonic imaging to obtain visible images of the region.

Still further, the present invention comprises a method for diagnosing the presence of diseased tissue in a patient, especially in the gastrointestinal region of the patient, said method comprising (i) administering to the patient one or more of the foregoing contrast media, and (ii) scanning the patient using ultrasonic imaging.

Finally, the present invention contemplates kits including the foregoing contrast media.

The present ultrasound contrast agents are particularly useful when employed in the gastrointestinal region, serving to improve visualization by displacing gas within the tract and providing contrast to the bowel lumen by filling it with material which has an echogenicity different from the adjacent mucosa.

These and other aspects of the invention will become more apparent from the following detailed description when taken in conjunction with the following drawings.

BRIEF DESCRIPTION OF THE DRAWINGS

In FIG. 3B, S denotes stomach, D denotes duodenum, and P denotes pancreas.

DETAILED DESCRIPTION OF THE INVENTION

Figure 1:
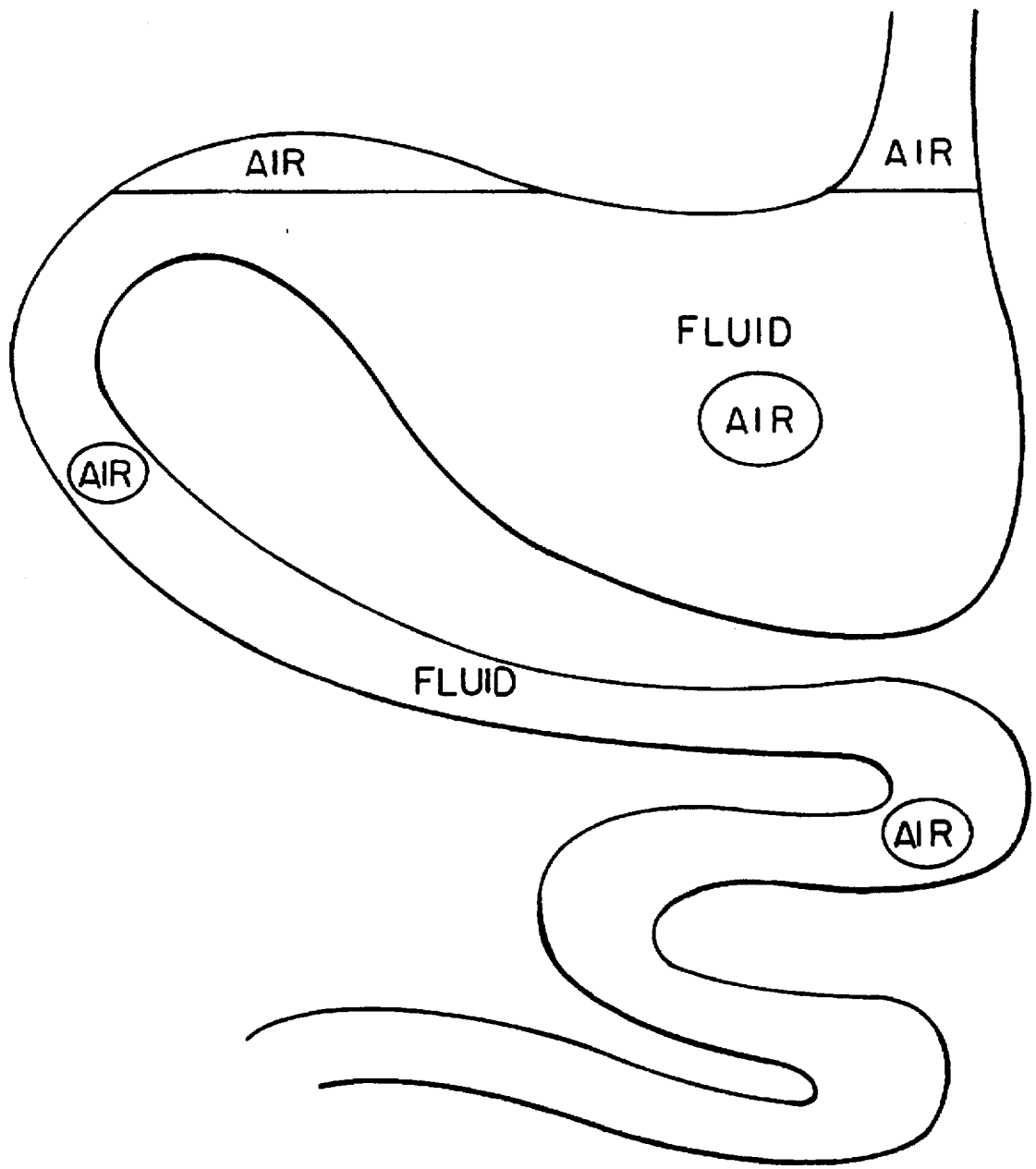
FIG. 1 is a diagrammatic view of a portion of the gastrointestinal tract of a patient showing representative air and fluid levels and air bubbles naturally present in the stomach and small intestines.
Figure 2A:
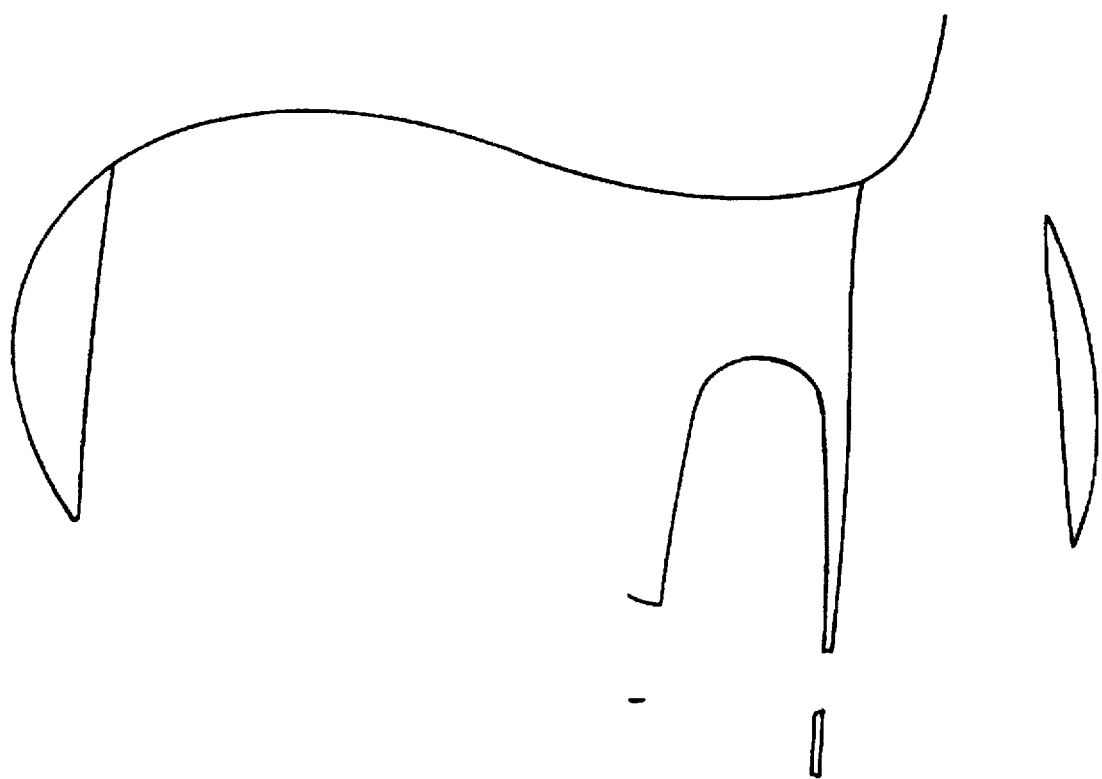
FIG. 2A is a diagrammatic view of a typical ultrasound image of the gastrointestinal tract of FIG. 1, showing the shadowing that results from air bubbles and air/fluid levels.
Figure 2B:
FIG. 2B is a typical photograph of an ultrasound image of the gastrointestinal tract of FIG. 1, showing the shadowing that results in the stomach from air bubbles and air/fluid levels.
Figure 2C:
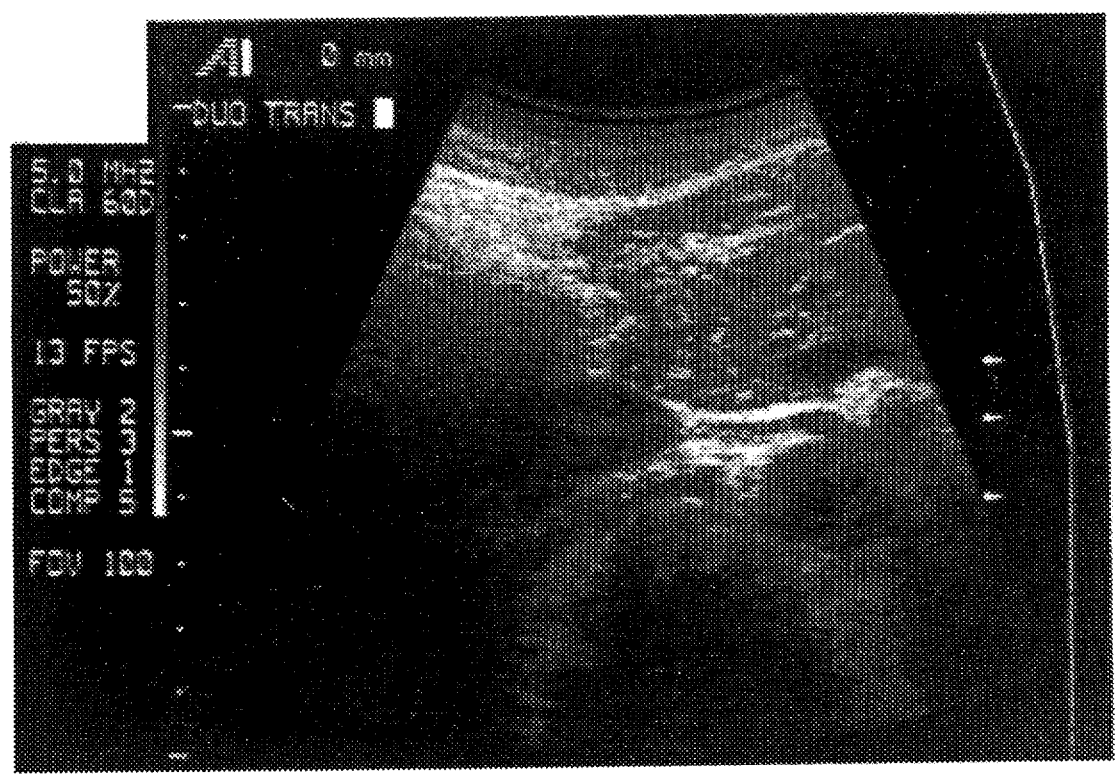
FIG. 2C is a typical photograph of an ultrasound image of the gastrointestinal tract of FIG. 1, showing the shadowing that results in a portion of the small intestine from air bubbles and air/fluid levels.
Figure 3A:
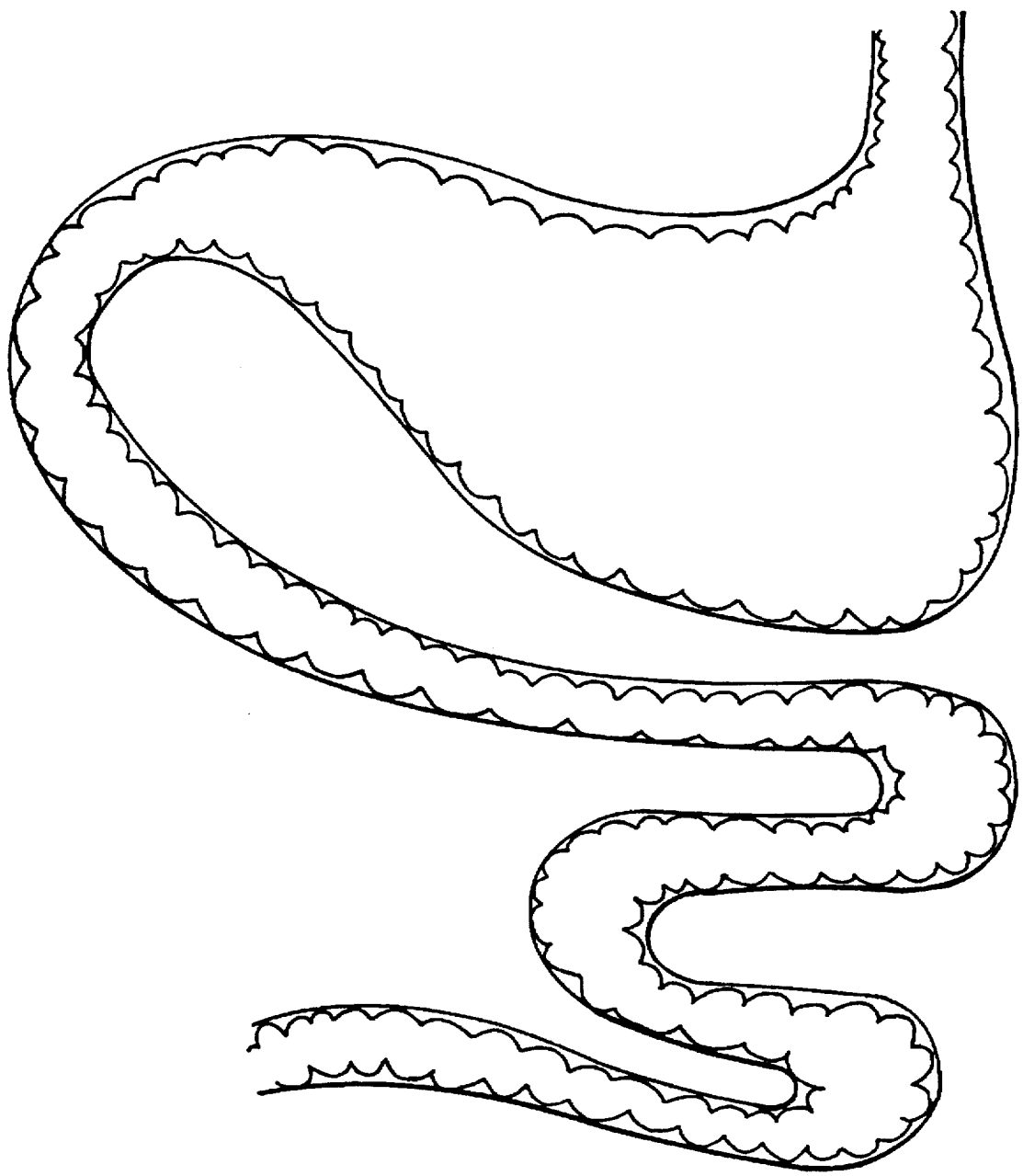
FIG. 3A is a diagrammatic view of an ultrasound image of the gastrointestinal tract of FIG. 1 after consumption of 750 ml of a 5% cellulose and 0.25% xanthan gum solution of the invention. Significant air/fluid levels and air bubbles are no longer present. Improved visualization of the gastrointestinal tract in general and improved visualization of the mucosa as distinguished from the tract lumen is observed.
Figure 3B:
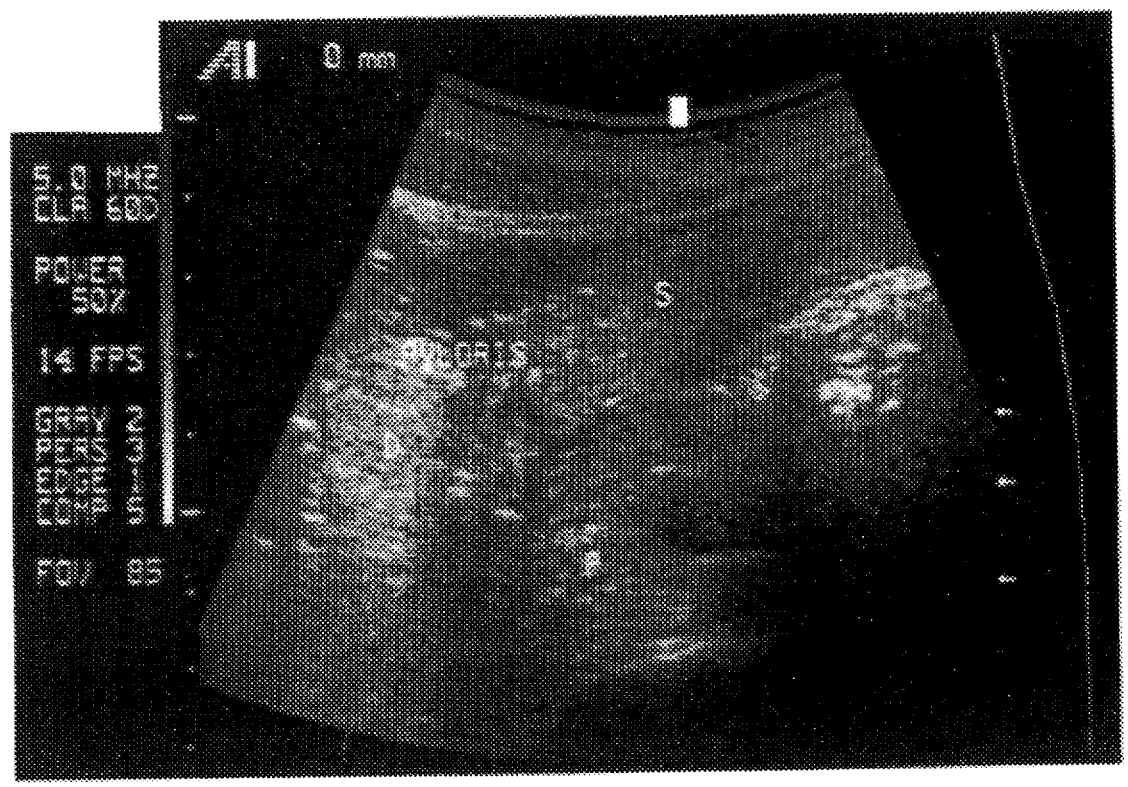
FIG. 3B is a photograph of an ultrasound image of the gastrointestinal tract of FIG. 1 after consumption of 750 ml of a 5% cellulose and 0.25% xanthan gum solution of the invention. Improved visualization of the gastro-intestinal tract in general and improved visualization of the mucosa as distinguished from the tract lumen is observed.

Any of the wide variety of biocompatible polymers known in the art may be employed in the medium and methods of the subject invention. The term biocompatible, used herein in conjunction with the term polymers, is employed in its conventional sense, that is, to denote polymers that do not substantially interact with the tissues, fluids and other components of the body in an adverse fashion in the particular application of interest. As will be readily apparent to those skilled in the art, there are numerous types of such polymers available.

The polymers useful in the present invention can be of either natural, semisynthetic or synthetic origin. As used herein, the term polymer denotes a compound comprised of two or more repeating monomeric units, and preferably 10 or more repeating monomeric units. The term semisynthetic polymer, as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galactocarolose, pectic acid, amylose, pullulan, glycogen, amylopectin, cellulose, dextran, pustulan, chitin, agarose, keratan, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine, and neuraminic acid, and naturally occurring derivatives thereof. Exemplary semisynthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes, polyethylene glycol, polyoxyethylene, polyethylene terephthalate, polypropylenes, polypropylene glycol, polyurethanes (such as, for example, polyether polyurethane ureas), pluronic acids and alcohols, polyvinyls (such as, for example, polyvinyl alcohol, polyvinylchloride and polyvinylpyrrolidone), nylon, polystyrene, polylactic acids, fluorinated hydrocarbons, fluorinated carbons (such as, for example, polytetrafluoroethylene), and polymethylmethacrylate, and derivatives thereof.

Preferably, the polymer employed is one which has a relatively high water binding capacity. When used, for example, in the gastrointestinal region, a polymer with a high water binding capacity binds a large amount of free water, enabling the polymer to carry a large volume of liquid through the gastrointestinal tract, thereby filling and distending the tract. The filled and distended gastrointestinal tract permits a clearer picture of the region. In addition, where imaging of the gastrointestinal region is desired, preferably the polymer employed is also one which is not substantially degraded within and absorbed from the gastrointestinal region. Minimization of metabolism and absorption within the gastrointestinal tract is preferable, so as to avoid the removal of the contrast agent from the tract as well as avoid the formation of gas within the tract as a result of this degradation. Moreover, particularly where gastrointestinal usage is contemplated, the polymers are preferably such that they are capable of displacing air and minimizing the formation of large air bubbles within the polymer composition.

In accordance with the invention, the polymers may be coated with and/or be in admixture with a silicon containing compound. As used herein, the phrase silicon containing compound denotes both organic and inorganic compounds containing the element silicon (Si). By admixture, it is meant that the silicon containing compound is simply added to the polymer containing medium, and is not chemically bound to the polymer. By the term coated, it is meant that the silicon containing compound is chemically bound to the polymer. Suitable silicon containing compounds include silicone, simethicones (such as simethicone and protected simethicone, the latter compound being polydimethylsiloxane with 4% to 4.5% silicon dioxide), siloxanes (such as polysiloxane, polydimethylsiloxane, polymethylvinylsiloxane, polymethylphenolsiloxane, polydiphenylsiloxane, octamethylcyclotetra-siloxane and siloxane glycol polymers), silanes (such as gamma-aminopropyltriethoxysilane, diethylaminomethyltriethoxysilane), silicon dioxide, siloxyalkylene polymers, linear or cyclic silazanes (such as hexadimethylsilazane, hexamethyldisilazane, hexaphenylcyclotrisilazane and octamethylcyclotetra-silazane), silyl compounds (such as N',N',-bis-(trimethylsilyl)acetamide and N-(dimethy(gamma-cyanopropyl)-silyl)-N-methylacetamide), and siliceous earth. Other suitable silicon compounds will be readily apparent to those skilled in the art, and are described, for example, in Hertl et al., *J. Phys. Chem.*, Vol. 75, No. 14, pp. 2182–2185 (1971). Such silicon compounds may be easily prepared using conventional chemical synthesis methodology, such as is described in *Chem. Abstracts*, Vol. 69, No. 61770x (1968), Vol. 70, No. 1164505k (1969), Vol. 74, No. 59904u (1971), Vol. 75, No. 9271v (1971), and Vol. 77, No. 37150q (1972), or may be obtained from various commercial sources. The silicon containing compounds surprisingly serve a number of important functions in the contrast medium, as both coating or admixed with the polymers, assisting in decreasing surface tension, minimizing foaming, increasing reflectivity, and/or lessening acoustic attenuation.

To prepare the biocompatible polymer coated with the silicon containing compound, a polymer reactive with the desired silicon containing compound is mixed therewith under conditions suitable for chemical bonding of the polymer and the silicon compound. Such reactive polymers and suitable conditions will be readily apparent to one skilled in the art, once in possession of the present disclosure. Suitable procedures include those described in Noll, *Chemistry and Technology of Silicones*, pp. 515–521 (Academic Press 1968), Hertl et al., *J. Phys. Chem.*, Vol. 75, No. 14, pp. 2182–2185 (1971), and Stark et al., *J. Phys. Chem.*, Vol. 72, No. 8, pp. 2750–2754 (1968), the disclosures of each of which are incorporated herein by reference in their entirety. Particularly reactive with many of the silicon containing compounds are polymers containing free hydroxyl groups, such as cellulose and polyethylene glycol.

Cellulose, a naturally occurring polymer that exhibits a high water binding capacity, when coated or admixed with a silicon containing compound, is particularly preferred for use in the subject invention, especially when gastrointestinal usage is desired, resulting in excellent echogenicity when ultrasound is applied. As a result of their high water binding capacity, the cellulosic compounds pass through the gastrointestinal tract in a liquid medium distending the tract and displacing gas within the tract. In addition, since cellulose is not degraded and absorbed within the tract, it does not result in the formation of any gases and is not removed from the tract along its route. Furthermore, cellulose is highly effective in displacing air and avoiding the formation of large air bubbles within the polymer composition. Polyvinylpyrrolidone, polyethylene glycol, and polyethylenes, when coated or admixed with a silicon containing compound, are also preferable polymers, particularly where gastrointestinal imaging is contemplated, functioning in a fashion similar to cellulose in binding water and distending the gastrointestinal tract, and resulting in highly improved visualization of the bowel and adjacent structures by ultrasound. Polyethylene glycol and polyethylenes are also very effective in preventing the formation of and in dispersing large gas bubbles. The silicon containing compounds employed with the foregoing polymers serve to decrease surface tension (thus allowing gas in the solution to escape more easily), minimize foaming, increase reflectivity, and/or lessen acoustic attenuation in the resultant contrast media.

The polymers of the present invention may be employed as solids in various shapes and forms, such as, for example, fibers, beads, and the like. As those skilled in the art will recognize, the size of the individual polymer fibers, beads, etc., can also vary widely. Preferably, however, the length of any polymer fibers and diameter of any polymer beads is between about 0.1 and about 200 microns, more preferably between about 5 and about 100 microns, most preferably between about 10 and about 20 microns. Fibers are preferred, and in general, shorter fiber lengths have been found to possess better acoustic properties and have better suspension uniformity than longer fiber lengths.

If desired, the polymers employed in the invention may be in liquid form, that is, liquid at physiological temperatures. The liquid polymer has its own inherent unique echogenicity which allows differentiation of bodily structures. Polyethylene glycol (PEG) of low molecular weight functions well in this regard (the lower molecular weight polymers being liquid at physiological temperatures) as do fluorinated hydrocarbons. As one skilled in the art will recognize, there are many polymers which are liquid at physiological temperatures and can be employed in this fashion.

The polymers of the invention may be employed in an aqueous solution as a contrast medium for ultrasound imaging.

If desired, in addition, the polymer solutions may be employed in conjunction with an additional anti-gas agent. As used herein the term anti-gas agent is a compound that serves to minimize or decrease gas formation, dispersion and/or adsorption. A number of such agents are available, including antacids, antiflatulents and antifoaming agents. Such antacids and antiflatulents include, for example, activated charcoal, aluminum carbonate, aluminum hydroxide, aluminum phosphate, calcium carbonate, dihydroxyaluminum sodium carbonate, magaldrate magnesium oxide, magnesium trisilicate, sodium carbonate, loperamide hydrochloride, diphenoxylate, hydrochloride with atropine sulfate, Kaopectate™ (kaolin) and bismuth salts. Suitable antifoaming agents useful as anti-gas agents include polyoxypropylenepolyoxyethylene copolymers, polyoxyalkylene amines and imines, branched polyamines, mixed oxyalkylated alcohols, sucroglycamides (celynols), polyoxylalkylated natural oils, halogenated silicon-containing cyclic acetals, lauryl sulfates, 2-lactylic acid esters of unicarboxylic acids, triglyceride oils. Particles of polyvinyl chloride may also function as anti-foaming agents in the subject invention. Of course, as those skilled in the art will recognize, any anti-gas agents employed must be suitable for use within the particular biological system of the patient in which it is to be used.

The polymer solutions may also, if desired, be employed with a suspending or viscosity increasing agent, referred to herein collectively as a suspending agent. The phrase suspending agent, as used herein, denotes a compound that assists in providing a relatively uniform or homogeneous suspension of polymer through out the aqueous solution. A number of such agents are available, including xanthum gum, acacia, agar, alginic acid, aluminum monostearate, unpurified bentonite, purified bentonite, bentonite magma, carbomer 934P, carboxymethylcellulose calcium, carboxymethylcellulose sodium, carboxymethylcellulose sodium 12, carrageenan, cellulose (microcrystalline), carboxymethylcellulose sodium, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide colloidal, sodium alginate, and tragacanth.

Wide variations in the amounts of the polymer, silicon containing compound, anti-gas agent, and suspending agent can be employed in the contrast medium of the invention. Preferably, however, the polymer, when employed in solid form, is present in an aqueous solution in a concentration of at least about 0.2% by weight, more preferably at least about 0.5% by weight, even more preferably at least about 1% by weight. Of course, as those skilled in the art would recognize, within these parameters, the optimum polymer concentration will be influenced by the molecular weight of the polymer, its water binding capacity, its particular echogenicity, as well as other characteristics of the particular polymer employed. In the case of cellulose, for example, the polymer is most preferably present in a concentration of between about 1% and about 5% cellulose by weight. When a medium to high molecular weight polyethylene glycol or polyvinylpyrrolidone is used as the polymer, the concentration is most preferably between about 1% to about 15% by weight. When the polymers are in liquid form, generally the polymer is present in a somewhat higher concentration, such as preferably in a concentration of at least about 10% by weight, more preferably at least about 20% by weight, even more preferably at least about 30% by weight. For example, when liquid polyethylene glycol is employed, the concentration is most preferably between about 10% and about 90% by weight. Similarly, when a liquid perfluorocarbon is used, the concentration is most preferably between about 1% and about 90% by weight. With respect to the silicon containing compound, preferably the concentration is between about 0.1% by weight and about 20% by weight, more preferably between about 0.5% by weight and about 10% by weight, most preferably between about 1% by weight and about 5% by weight, whether present as a coating (that is, chemically bound to the polymer) or as an admixture (that is, added to the polymer medium but not chemically bound to the polymer). Generally, because of an increased ability to remain in a homogeneous suspension, the lower amounts of silicon containing compound are preferred.

In a preferably embodiment, the contrast medium of the invention is degassed, most preferably by either autoclaving the contrast medium, or by sonicating the contrast medium under vacuum (processes which forces gas out of solution as well as sterilizes the product), and then bottling the contrast medium under vacuum. The vacuum bottling is used so as to keep any new gas bubbles from forming in the product. The degassing and vacuum bottling serves to enhance the ultimate ecogenicity and minimize shadowing when the contrast medium is employed in vivo.

If desired, an antimicrobial agent may be included in the contrast medium to prevent bacterial overgrowth in the medium. Antimicrobial agents which may be employed include benzalkonium chloride, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

The present invention is useful in imaging a patient generally, and/or in specifically diagnosing the presence of diseased tissue in a patient. The imaging process of the present invention may be carried out by administering a contrast medium of the invention to a patient, and then scanning the patient using ultrasound imaging to obtain visible images of an internal region of a patient and/or of any diseased tissue in that region. By region of a patient, it is meant the whole patient, or a particular area or portion of the patient. The contrast medium is particularly useful in providing images of the gastrointestinal region, but can also be employed more broadly such as in imaging any body cavities, or in other ways as will be readily apparent to those skilled in the art, such as in imaging the vasculature, liver, and spleen, and for use in tissue characterization. The phrase gastrointestinal region or gastrointestinal tract, as used herein, includes the region of a patient defined by the esophagus, stomach, small and large intestines and rectum. By body cavities it is meant any region of the body having an open passage, either directly or indirectly, to the external environment, such regions including the gastrointestinal region, the sinus tract, the fallopian tubes, etc. The patient can be any type of mammal, but most preferably is a human. Any of the various types of ultrasound imaging devices can be employed in the practice of the invention, the particular type or model of the device not being critical to the method of the invention.

As one skilled in the art would recognize, administration of the contrast medium to the patient may be carried out in various fashions, such as orally, rectally or by injection. When the region to be scanned is the gastrointestinal region, administration of the contrast medium of the invention is preferably carried out orally or rectally. When other body cavities such as the fallopian tubes or sinus tracts are to be scanned, administration is preferably by injection. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. By way of guidance, for gastrointestinal usage, about 10 ml of contrast medium per kg weight of the patient is administered (that is, a 70 kg patient would be administered about 700 ml of contrast medium). Various combinations of biocompatible polymers, silicon containing compounds, anti-gas agents, suspending agents, and other agents may be used to modify the echogenicity or ultrasonic reflectance of the gastrointestinal contrast agent, as well as to achieve the desired viscosity, gastric transit time, osmolality and palatability.

In carrying out the method of the present invention, the contrast medium can be used alone, or in combination with other diagnostic, therapeutic or other agents. Such other agents include flavoring or coloring materials, antioxidants, anticaking agents (to prevent caking on settling), tonicity agents (to optionally adjust osmolality to be iso-osmotic), and wetting agents (to facilitate mixing of the components in the contrast medium). Flavoring materials include, for example, aspartame, dextrates, dextrose, dextrose excipient, fructose, mannitol, saccharin, saccharin calcium, saccharin sodium, sorbitol, sucrose, sugar (compressible), and sugar (confectioner's syrup). Coloring materials include, for example, caramel and ferric oxide (e.g., red, yellow, black, or blends thereof). Antioxidants include, for example, ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide tocopherol, and tocopherols excipient. Anticaking agents include, for example, calcium silicate, magnesium silicate, and silicon dioxide (either colloidal or talc). Tonicity agents include, for example, dextrose, glycerin, mannitol, potassium chloride, sodium chloride, and propylene glycol. Wetting agents include, for example, benzalkonium chloride, benzethonium chloride, cetylpyridinium chloride, docusate sodium, nonoxynol 9, nonoxynol 10, octoxynol 9, polyoxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, and tyloxapol. The foregoing additional agents are conventional, and are described, for example, in the *U.S. Pharmacopeia National Formulary*, 22nd Revision, Jan. 1, 1990, Mack Printing Company, Easton, PA.

The media of the present invention have been shown to be extremely useful as contrast enhancement agents in ultrasonic imaging, particularly in imaging of the gastrointestinal region.

Kits useful for ultrasonic imaging in accordance with the present invention comprise a contrast medium of the present invention, that is, an aqueous solution of at least one biocompatible polymer, wherein said biocompatible polymer is coated with and/or in admixture with at least one silicon containing compound, in addition to conventional ultrasonic imaging kit components. Such conventional ultrasonic imaging kit components are well known, and include, for example, anti-gas agents, suspending agents, flavoring materials, coloring agents and antioxidants, as described above.

A particularly preferred formulation of the contrast medium of the present invention useful in ultrasonic imaging, particularly of the gastrointestinal region, is a degassed solution comprised of the following components:

(i) 0.5% by weight of an 18 micron fiber length cellulose polymer coated with 0.25% by weight of the silicon containing compound simethicone;

(ii) 500 ppm of the silicon containing compound simethicone in admixture with the polymer in (i);

(iii) 100 ppm of the anti-gas agent lauryl sulfate;

(iv) 0.3% by weight xanthan gum; and (v) optionally, the flavoring agent Vivonex™ (commercially available from Norwhich Eaton Pharmaceutical Inc., Norwhich, N.Y.).

The present invention is further described in the following Examples. In the Examples which follow, the polymers described are in the form of solid fibers, with any sizes given denoting fiber length. The Examples are not to be construed with as limiting the scope of the appended claims.

EXAMPLES

Example 1

Surface tension, foaming and bubble formation was measured for various contrast media comprising biocompatible polymers, both (i) with coating and/or in admixture with a silicon containing compound, and (ii) without coating and/or in admixture with a silicon containing compound. In some cases anti-gas agents and/or suspending agents were included in the contrast media tested. All samples were freshly degassed prior to use by sonication using a commercially available sonicator (Bransen, 2200 Danbury, Conn.) under vacuum using a commercially available vacuum pump (Cole Parmer Model No. 7049–50, Chicago, Ill.).

Surface tension measurements were performed a 25° C. using a CSC-DuNouy tensiometer No. 70535 (Fairfax, Va.). Degree of foaming was assessed by shaking the freshly degassed solutions in 50 cc plastic tubes (Fisher Scientific 05-539-8; Pittsburgh, Pa.). A volume of 25 cc of each contrast agent suspension was placed in the tube and the tubes were capped. The tubes were then shaken vigorously for 60 seconds and the degree of foaming was assessed at a time-point (60 seconds) after the shaking ceased. Foam was recorded on the scale of 0=no foam, 1=minimal foam (about 1 mm), 2=moderate foam (about 2 to 3 mm), 3=severe foaming (more than 4 mm). The bubbles in the suspensions were assessed similarly after shaking but the bubbles were counted only within the suspensions, not as the foam which was determined by assessing the layer at the top of the suspension. Bubbles within the suspensions were assessed by examining the bubbles and grading them as 0=no bubbles, 1=small bubbles (<1 mm diameter with very few bubbles), 2=medium bubbles (1–2 mm diameter and few to moderate bubbles), and 3=large bubbles (>2 mm diameter with many bubbles).

The data from the surface tension, foaming, and bubble measurements are set forth in the Tables I–III. As shown in Table I, cellulose functions as a mild surfactant (that is, its surface tension is less than water), when the cellulose is prepared alone. When xanthan gum is added to the cellulose, this causes the mixture to lose some of its favorable surfactant properties and the surface tension is similar to water. Polyethylene glycol (PEG 3350) has low surface tension and no foaming (but note in Example 2, that PEG has no appreciable reflectivity on ultrasonic study). Methylcellulose caused appreciable foaming. Simethicone coated cellulose, on the other hand, has low surface tension, no appreciable foaming, and no appreciable bubbles.

TABLE I

Effect of Simethicone/Silicone Coatings/Admixtures on Surface Tension, Foaming and Bubble Formation

| | Dynes/cm | Foam | Bubbles |
|---|---|---|---|
| Deionized Water | 73.5 | 0.0 | 0.0 |
| 18µ Cellulose | | | |
| 1% cellulose | 71.3 | 0.0 | 0.0 |
| 2% cellulose | 71.2 | 0.0 | 0.0 |
| 18µ cellulose | | | |
| w/0.25% xanthan gum | | | |
| 1% cellulose | 72.7 | 0.0 | 1.0 |
| 2% cellulose | 72.8 | 0.0 | 1.0 |
| 18µ cellulose | | | |
| w/0.05% xanthan gum | | | |
| 1% cellulose | 71.6 | 0.0 | 0.5 |
| 2% cellulose | 72.0 | 0.0 | 0.05 |
| 18µ cellulose | 70.6 | 0.0 | 0.0 |
| 1% simethicone coated | | | |
| 0.25% xanthan gum | | | |
| 18µ cellulose | 70.3 | 0.0 | 0.0 |
| 1% silicone coated | | | |
| 0.25% xanthan gum | | | |
| 1% cellulose | 61.0 | 0.0 | 0.0 |
| 1% silicone coated | | | |
| 2% cellulose | 61.8 | 0.0 | 0.0 |
| 1% silicone coated | | | |
| 1% cellulose | 62.0 | 0.0 | 0.0 |
| 1% simethicone coated | | | |
| 2% cellulose | 61.0 | 0.0 | 0.0 |
| 1% simethicone coated | | | |

Key:
Foam 0.0–3.0
Bubbles 0.0–3.0
(for foam and bubbles, zero is the most favorable)
Dynes (20.0–80.0)
(for dynes, the lower the number, the better)

TABLE II

Effect of Anti-Gas Agents on Surface Tension, Foaming and Bubble Formation of Simethicone/Silicone Coatings/Admixtures

|  | Dynes/cm | Foam | Bubbles |
|---|---|---|---|
| Sodium lauryl sulfate w/ 1% 18μ 1% silicone coated cellulose w/ 0.15% xanthan gum | | | |
| 100 ppm sodium lauryl sulfate | 49.1 | 1.0 | 1.0 |
| 500 ppm sodium lauryl sulfate | 34.4 | 2.0 | 1.5 |
| Sodium lauryl sulfate w/ 1% 18μ 1% silicone coated cellulose w/ 0.15% xanthan gum | | | |
| 100 ppm sodium lauryl sulfate | 52.2 | 1.0 | 1.0 |
| 500 ppm sodium lauryl sulfate | 35.1 | 2.0 | 1.5 |
| 1000 ppm Simethicone w/500 ppm sodium lauryl sulfate w/ 1% 18μ 1% silicone coated cellulose w/ 0.15% xanthan gum | 32.9 | 0.0 | 0.0 |

Key:
Foam 0.0–3.0
Bubbles 0.0–3.0
(for foam and bubbles, zero is the most favorable)
Dynes (20.0–80.0)
(for dynes, the lower the number, the better)

TABLE III

Comparison of Various Polymer Compositions in Surface Tension, Foaming and Bubble Formation

|  | Dynes/cm | Foam | Bubbles |
|---|---|---|---|
| Deionized Water | 73.5 | 0.0 | 0.0 |
| 18μ Cellulose | | | |
| 1% cellulose | 71.3 | 0.0 | 0.0 |
| 2% cellulose | 71.2 | 0.0 | 0.0 |
| Polyethylene Glycol (PEG3350) (Not Degassed) | | | |
| 1% PEG | 63.3 | 0.0 | 0.0 |
| 2% PEG | 62.8 | 0.0 | 0.0 |
| 3% PEG | 63.1 | 0.0 | 0.0 |
| 4% PEG | 62.8 | 0.0 | 0.0 |
| 5% PEG | 62.4 | 0.0 | 0.0 |
| Polyethylene Glycol (PEG3350) (Degassed) | | | |
| 1% PEG | 62.3 | 0.0 | 0.0 |
| 2% PEG | 62.1 | 0.0 | 0.0 |
| 3% PEG | 61.6 | 0.0 | 0.0 |
| 4% PEG | 61.5 | 0.0 | 0.0 |
| 5% PEG | 61.2 | 0.0 | 0.0 |
| 18μ Cellulose w/0.25% Xanthan Gum | | | |
| 1% cellulose | 72.7 | 0.0 | 1.0 |
| 2% cellulose | 72.8 | 0.0 | 1.0 |
| 3% cellulose | 73.1 | 0.0 | 1.0 |
| 4% cellulose | 72.8 | 0.0 | 1.0 |
| 5% cellulose | 73.0 | 0.0 | 1.0 |
| 18μ Cellulose w/0.05% Xanthan Gum | | | |
| 1% cellulose | 71.6 | 0.0 | 0.5 |
| 2% cellulose | 72.0 | 0.0 | 0.5 |
| 3% cellulose | 71.7 | 0.0 | 0.5 |
| 4% cellulose | 71.8 | 0.0 | 0.5 |
| 5% cellulose | 71.9 | 0.0 | 0.5 |
| Polyethylene Glycol (PEG3350) w/1% 18μ Cellulose w/0.15% Xanthan Gum | | | |
| 1% PEG | 54.1 | 0.0 | 1.5 |
| 2% PEG | 51.2 | 0.0 | 1.5 |
| 3% PEG | 56.0 | 0.0 | 1.5 |
| 18μ Cellulose 1% Simethicone Coated w/0.25% Xanthan Gum | 70.6 | 0.0 | 0.0 |
| 18μ Cellulose 2% Silicone Coated 0.25% Xanthan Gum | 70.3 | 0.0 | 0.0 |
| Propylene Glycol w/1% 18μ 1% Silicone Coated Cellulose w/ 0.15% Xanthan Gum | | | |
| 3% PG | 61.8 | 0.0 | 1.0 |
| 5% PG | 62.0 | 0.0 | 1.5 |
| Sodium Lauryl Sulfate w/1% 18μ 1% Silicone Coated Cellulose w/0.15% Xanthan Gum | | | |
| 100 ppm SLS | 49.1 | 1.0 | 1.0 |
| 500 ppm SLS | 34.4 | 2.0 | 1.5 |
| Sodium Lauryl Sulfate w/2% Polyethylene Glycol (PEG3350) w/1% 18μ 1% Silicone Coated Cellulose w/0.15% Xanthan Gum | | | |
| 100 ppm SLS | 51.5 | 1.0 | 1.5 |
| 500 ppm SLS | 34.5 | 2.0 | 2.0 |
| Sodium Lauryl Sulfate w/1% 18μ 1% Silicone Coated Cellulose w/0.15% Xanthan Gum | | | |
| 100 ppm SLS | 52.2 | 1.0 | 1.0 |
| 500 ppm SLS | 35.1 | 2.0 | 1.5 |
| Simethicone w/500 ppm Sodium Lauryl Sulfate w/1% 18μ Silicone Coated Cellulose w/0.15% Xanthan Gum | 32.9 | 0.0 | 1.0 |
| 1000 ppm simethicone 1% 18μ 1% Simethicone Coated Cellulose w/500 ppm | | | |

TABLE III-continued

Comparison of Various Polymer Compositions in Surface Tension, Foaming and Bubble Formation

|  | Dynes/cm | Foam | Bubbles |
|---|---|---|---|
| Sodium Lauryl Sulfate w/1000 ppm Simethicone w/0.15% Xanthan Gum | | | |
| #1 | 30.8 | 1.5 | 1.5 |
| #2 | 33.1 | 1.0 | 1.5 |
| #3 | 33.2 | 1.0 | 1.5 |
| #4 | 33.2 | 0.5 | 1.5 |
| #5 | 32.9 | 0.5 | 1.5 |
| #6 | 33.2 | 0.5 | 1.5 |
| #7 | 32.8 | 0.5 | 1.5 |
| #8 | 33.1 | 0.5 | 1.5 |
| #9 | 32.1 | 0.5 | 1.5 |
| Methyl Cellulose | | | |
| 0.15% | 54.6 | 2.0 | 0.0 |
| 0.25% | 53.9 | 2.5 | 0.0 |
| 0.50% | 54.1 | 2.5 | 0.0 |
| 1.00% | 54.5 | 3.0 | 0.0 |
| Hydroxyethyl Cellulose (Natrasol ™) | | | |
| 0.15% | 64.0 | 2.0 | 0.0 |
| 0.25% | 56.1 | 1.5 | 0.5 |
| 0.50% | 51.7 | 1.0 | 1.5 |
| 1.00% | 50.4 | 0.5 | 2.5 |
| Carrageenan | | | |
| 0.15% | 72.9 | 0.0 | 0.0 |
| 0.25% | 72.6 | 0.0 | 0.0 |
| 0.50% | 72.8 | 0.0 | 0.5 |
| Xanthan Gum | | | |
| 0.15% | 72.8 | 0.0 | 0.5 |
| 0.25% | 73.6 | 0.0 | 1.0 |
| 0.50% | 73.1 | 0.0 | 1.0 |
| 1.00% | 75.9 | 0.0 | 1.5 |
| Carboxymethyl Cellulose | | | |
| 0.15% | 72.0 | 0.0 | 0.5 |
| 0.25% | 72.4 | 0.0 | 1.0 |
| 0.50% | 72.4 | 0.0 | 1.5 |
| 1.00% | 73.3 | 0.0 | 2.0 |
| Sodium Lauryl Sulfate | | | |
| 100 ppm | 51.4 | 1.0 | 0.0 |
| 200 ppm | 48.6 | 1.5 | 0.0 |
| 300 ppm | 35.7 | 2.0 | 0.0 |
| 400 ppm | 29.8 | 2.5 | 0.0 |
| 500 ppm | 29.5 | 3.0 | 0.0 |
| Corn Starch w/0.15% Xanthan Gum | | | |
| 1% corn starch | 73.0 | 0.0 | 0.0 |
| 3% corn starch | 73.1 | 0.0 | 0.0 |
| 5% corn starch | 73.1 | 0.0 | 0.0 |
| Wheat (Cook-up) Starch w/0.15% Xanthan Gum | | | |
| 1% wheat starch | 72.2 | 0.0 | 1.5 |
| 3% wheat starch | 71.0 | 0.0 | 2.0 |
| 5% wheat starch | 69.7 | 0.0 | 2.5 |
| Wheat (Instant) Starch w/0.15% Xanthan Gum | | | |
| 1% wheat starch | 59.9 | 0.0 | 2.0 |
| 3% wheat starch | 56.7 | 0.0 | 2.0 |
| 5% wheat starch | — | 0.0 | 2.5 |
| 1% 18μ 1% Simethicone Coated Cellulose w/0.30% Xanthan Gum (Keltrol RD ™) | 37.6 | 0.0 | 0.0 |
| w/100 ppm Sodium Lauryl Sulfate | | | |
| w/500 ppm Simethicone w/0.5% flavoring | | | |

Key:
Foam 0.0–3.0
Bubbles 0.0–3.0
(for foam and bubbles, zero is the most favorable)
Dynes (20.0–80.0)
(for dynes, the lower the number, the better)

Example 2

Velocity, acoustic impedance, dB reflectivity, and attenuation was measured for various contrast media comprising biocompatible polymers, both (i) with coating and/or in admixture with a silicon containing compound, and (ii) without coating and/or in admixture with a silicon containing compound.

The dB reflectivity of the different contrast agents was assessed with an Acoustic Imaging Model 5200 ultrasound scanner (Phoenix, Ariz.) equipped with Performance Software PFM. The transducers, either 5.0 or 7.5 Mhz, were placed in the contrast agents and scanned. Prior to performing each set of experiments the dB reflectivity was standardized to a known reference phantom. For the dB reflectivity measurements on the Acoustic Imaging 5200, a tissue mimicking phantom was used as a reference. The tissue mimicking phantom is made by Nuclear Associates. The gain was set to −53.5 dB. The dB reflectivity measurements were made by selecting a region of interest on the CRT monitor and reading the mean dB reflectivity in that region. Quantitative measurements of samples were obtained on a benchtop acoustic lab custom built by ImaR$_x$, (Tucson, Ariz.), consisting of a Panametric (Waltham, Mass.) 5052PR ultrasonic pulser/receiver, LeCroy (Chestnut Ridge, N.Y.) 9410 dual channel digital oscilloscope with a waveform processing package and capabilities of Fast Fourier Transform and Krautkramer Branson (Lewistown, Pa.), F-style, Gamma-HP series transducers. Data was obtained using the pulse-echo technique. The returned echoes were measured with the appropriate time delays and the power average of the waveform was calculated. The frequencies of the transducers used were 2.25, 3.25, 5.0, 7.5 and 10 mHz. The ultrasonic waves were reflected from a solution/air interface reflected from a solution/air interface. Parameters of velocity, acoustic impedance, attenuation and transmittance were assessed.

As shown by the data, cellulose with simethicone coating has both good reflectivity and very high transmission (that is, less acoustic attenuation) than plain cellulose. Note also that polyethyleneglycol has much lower reflectivity than cellulose.

Figure 4:
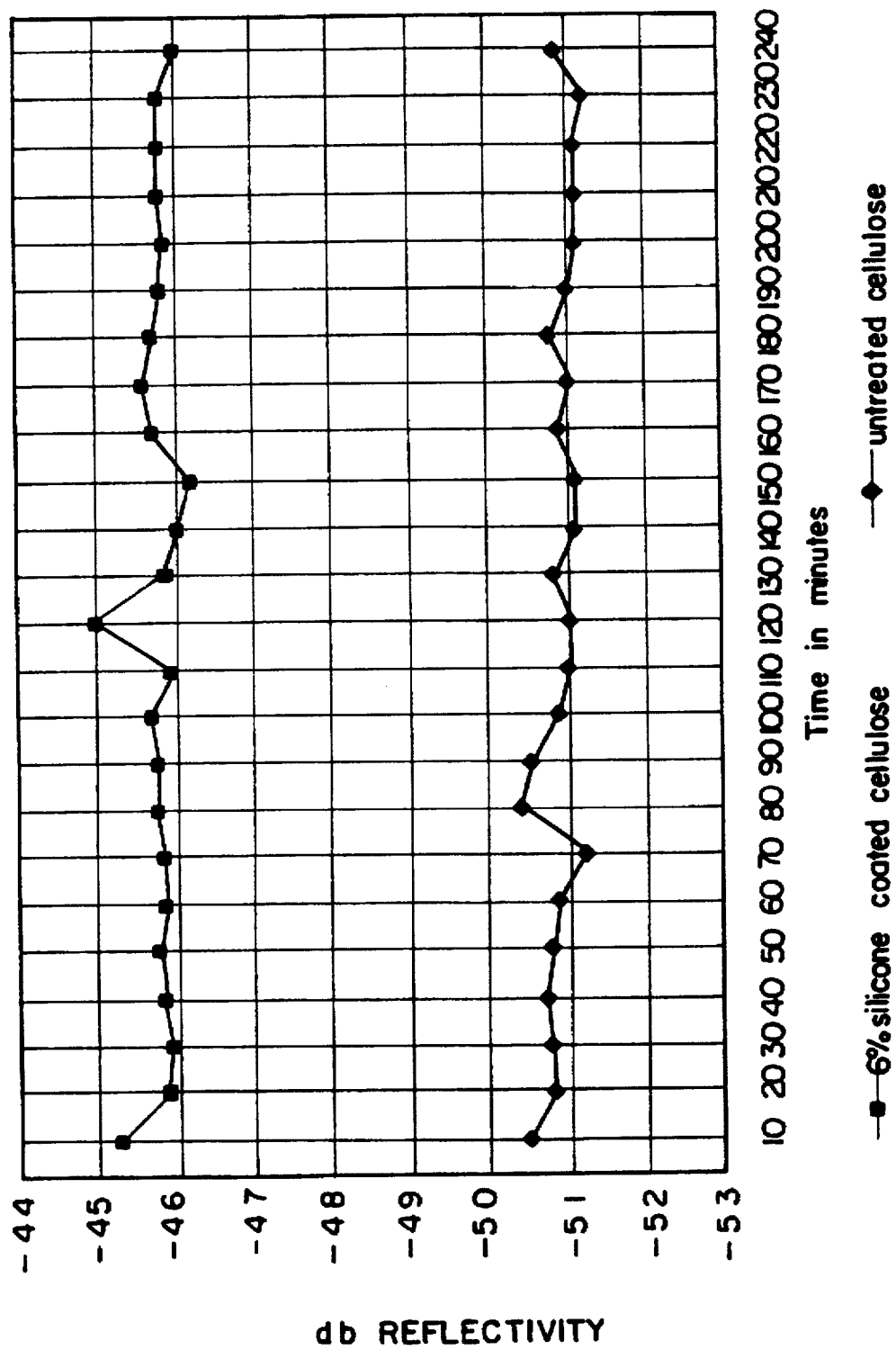
FIG. 4 is a graph showing the dB reflectivity of cellulose coated with silicone and uncoated cellulose in vitro. The coated cellulose exhibits a significantly better dB reflectivity.
Figure 5:
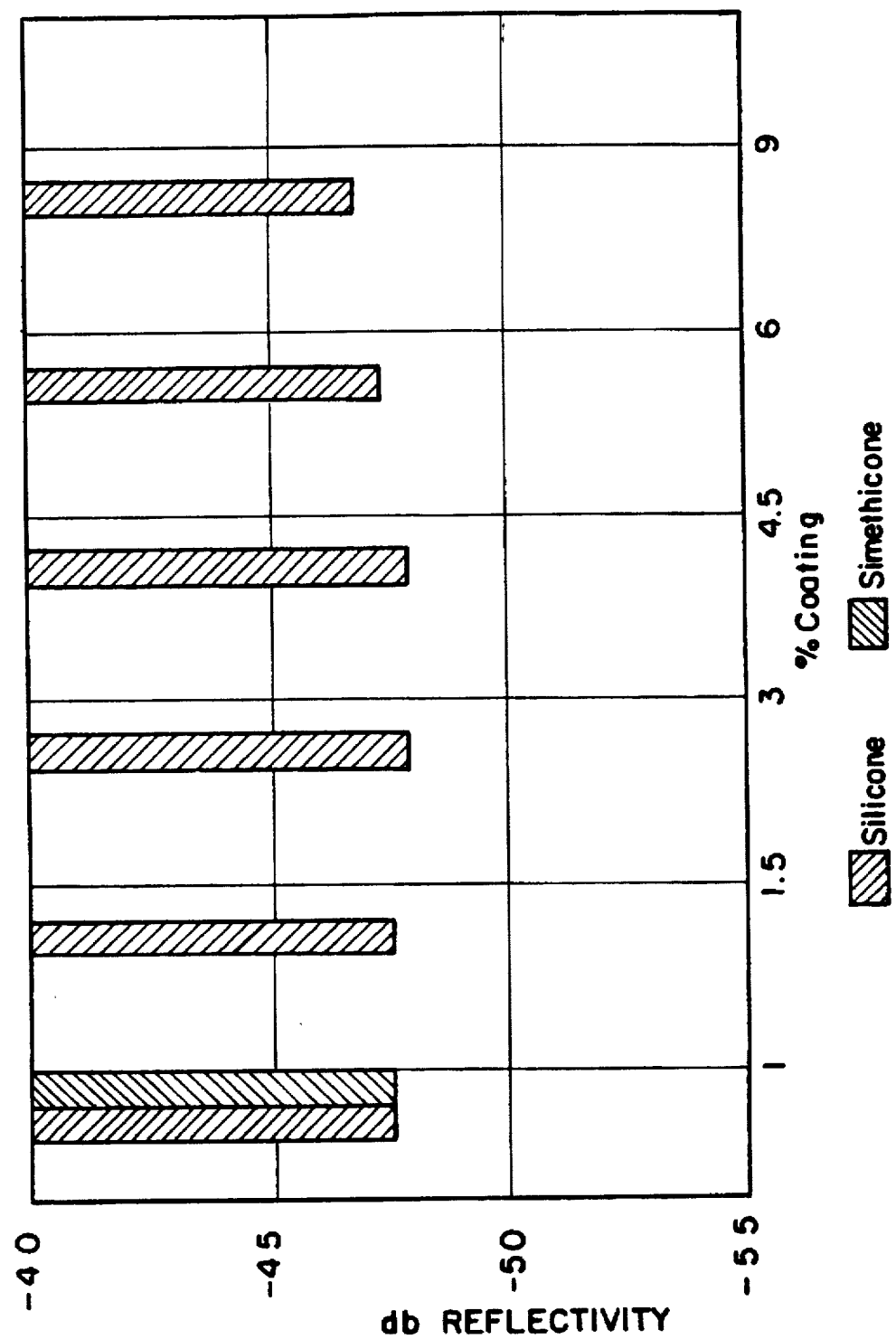
FIG. 5 is a graph showing the dB reflectivity of cellulose fibers 18μ in length coated with varying amounts of silicone and simethicone in vitro.
Figure 6:
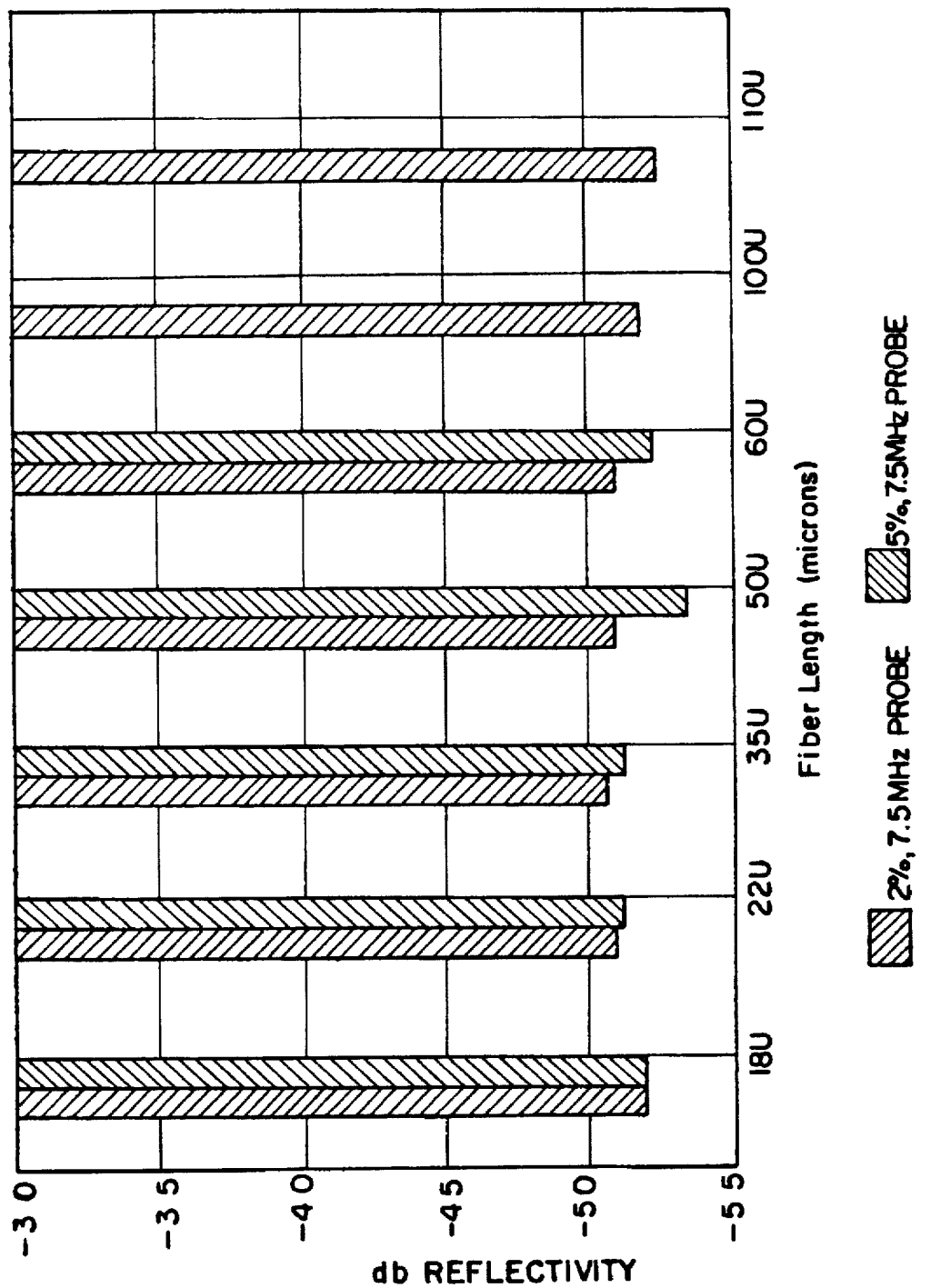
FIG. 6 is a graph showing the dB reflectivity of uncoated cellulose fibers of varying length at different concentrations of cellulose and different transducer frequencies in vitro.
Figure 7:
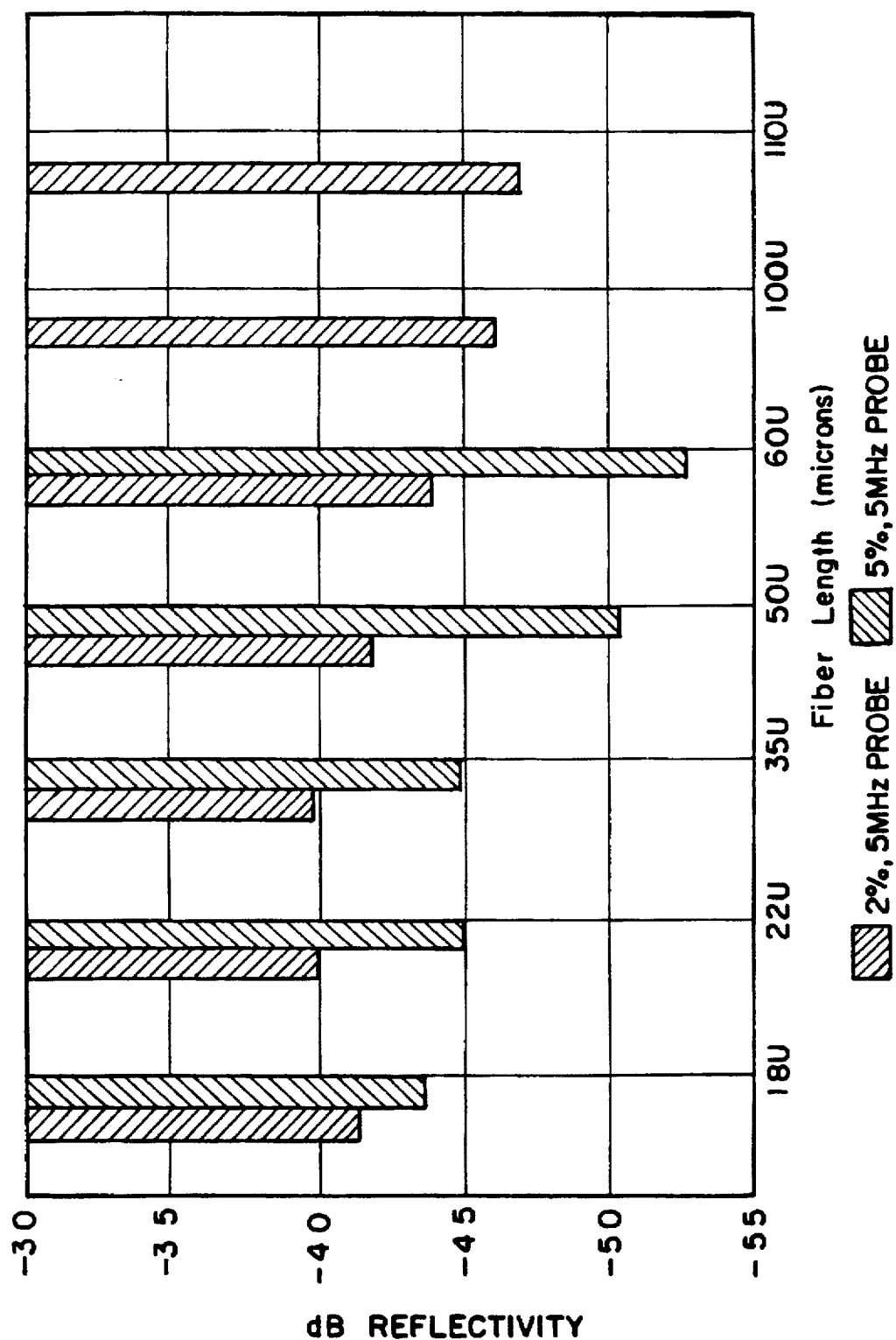
FIG. 7 is a graph showing the dB reflectivity of uncoated cellulose fibers of varying length at different concentrations of cellulose and different transducer frequencies in vitro.
Figure 8:
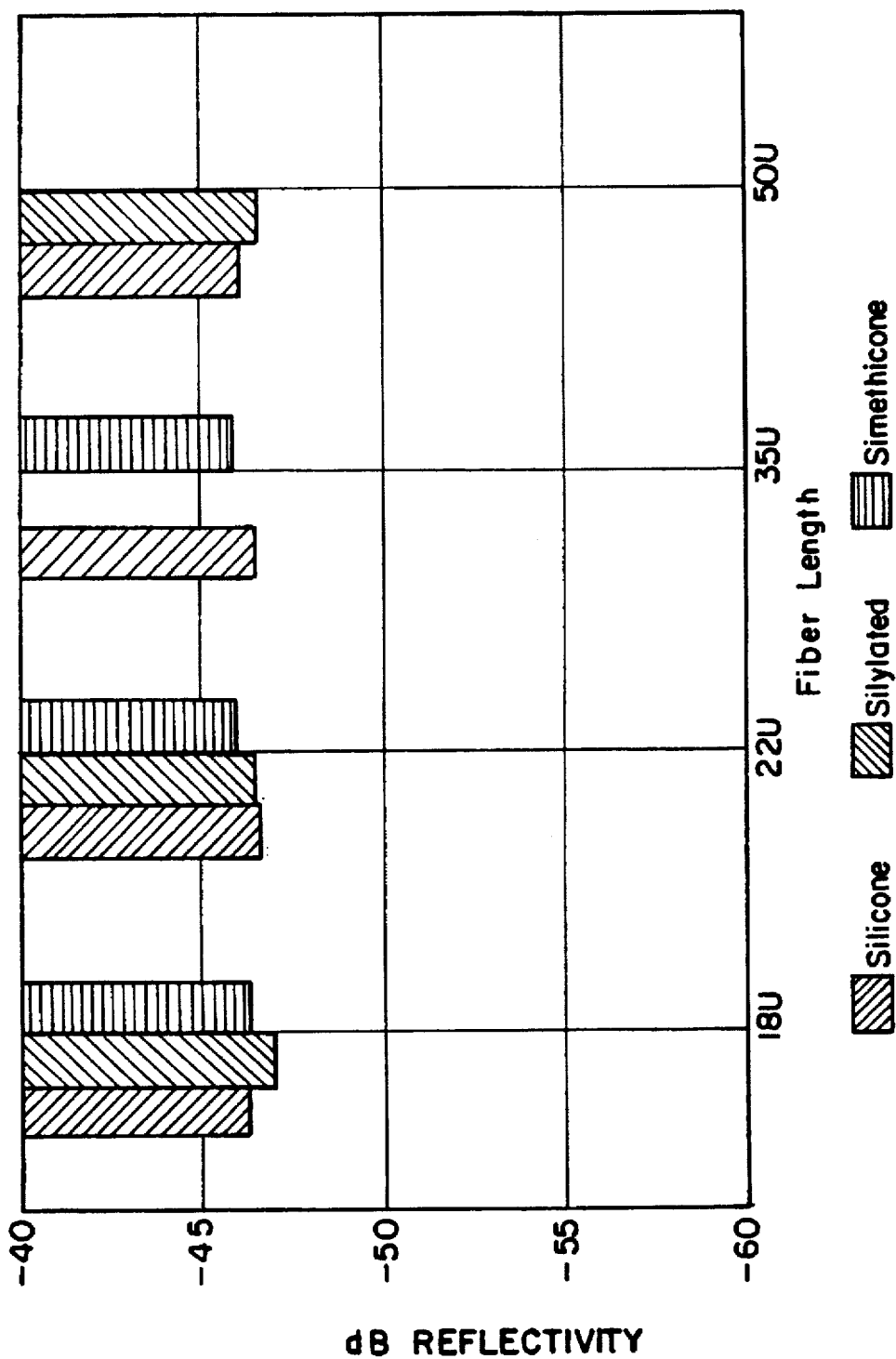
FIG. 8 is graph showing the dB reflectivity of cellulose fibers of varying length coated with 1% of different silicon compounds in vitro.

FIGS. 4–8 show the dB reflectivity from the measurements made on the phantoms with the Acoustic Imaging Ultrasound machine. As shown by these figures, for plain cellulose the shorter fibers (e.g. 18 through 35 micron) have higher reflectivity than the longer cellulose fibers. Note that the silicone coated cellulose has higher reflectivity than the uncoated fibers.

Example 3

Hexamethyldisilazane (1,1,1,3,3,3-hexamethyldisilazane) (2 g), commercially available from Aldrich Chemical Company, Milwaukee Wis., was added to 10 g of ethyl alcohol (200 proof dehydrated alcohol, U.S.P. punctilious). The hexamethyldisilazane and ethyl alcohol mixture was then added drop by drop to 28.5 g of cellulose (fiber lengths 18μ, 22μ, and 35μ, respectively) in a flask. The mixture was stirred and heated at a temperature of about 60° C. in a vacuum oven. After the ethyl alcohol was evaporated, the flask was placed into a laboratory oven and heated from about 60° C. to about 140° C. for about two hours and then cooled, resulting in hexamethyldisilazane coated cellulose (also referred to herein generally as silylated cellulose).

Example 4

Silicone (in oil form) (2 g), commercially available from Aldrich Chemical Co. Inc., was added to 10 g of toluene. The silicone and toluene mixture was then added drop by drop to 28.5 g of cellulose in a flask. The mixture was stirred and heated at a temperature of about 60° C. in a vacuum oven. After the toluene was evaporated, the flask was placed into a laboratory oven and heated from about 60° C. to about 140° C. for about two hours and then cooled, resulting in silicone coated cellulose.

Example 5

A solution containing about 15% by weight polyethylene glycol fibers having a molecular weight of about 8000 was prepared in deionized water. The solution was then mixed with a gas and the solution was scanned in vitro by ultrasound.

The polyethylene glycol polymer solution was found to improve gas dissipation and render a good image on in vitro scanning.

Example 6

Three solutions containing about 5% by weight cellulose fibers having varying fiber lengths of cellulose of about 22, 60, and 110 microns, respectively, and each containing about 0.25% xanthan gum were prepared in distilled water. A fourth solution containing about 5% by weight dextran beads of about 20 micron diameter was prepared in distilled water. The solutions were scanned in vitro by ultrasound at constant gain settings using a 5 megahertz transducer (approximately a 300 micron wave length in aqueous media).

The 20 micron diameter dextran bead solution had the highest echogenicity of the four solutions, with the 22 micron fiber length cellulose solution having the next highest echogenicity.

Example 7

A solution containing about 5% by weight cellulose fibers having a fiber length of about 22 microns and about 0.25% by weight xanthan gum was prepared in deionized water. Approximately 750 ml of the solution was then administered orally to a mammal, and ultrasonic imaging of the gastrointestinal tract was performed.

Distention of the gastrointestinal tract and good visualization of the gastrointestinal region was achieved. Excellent visualization of the mucosal surfaces of the stomach and intestine was also achieved.

Example 8

A solution containing about 4% by weight cellulose fibers having a fiber length of about 22 microns and about 2 g of activated charcoal in deionized water was prepared. Approximately 750 ml of the solution was then administered orally to a mammal and ultrasonic imaging of the gastrointestinal tract was performed.

Ultrasonic imaging provided good visualization of the tract and mucosal surfaces.

Example 9

A solution containing about 5% by weight cellulose fibers having a fiber length of about 22 microns and about 0.25% by weight xanthan gum was prepared in deionized water. To this solution, about 2.0 g of simethicone was added and the solution was mixed. Approximately 750 ml of the solution was then administered orally to a mammal, and ultrasonic imaging of the gastrointestinal tract was performed.

Ultrasonic imaging provided good visualization of the tract and mucosal surfaces. In addition, improved removal of gas bubbles from the gastrointestinal tract was observed.

Various modifications of the invention in addition to those shown and described herein will be apparent to those skilled in the art from the foregoing description. Such modifications are also intended to fall within the scope of the appended claims.

What is claimed is:

1. A contrast medium for ultrasonic imaging comprising an aqueous suspension of at least one biocompatible natural or modified natural polymer in combination with and separate from at least one anti-gas agent, wherein said biocompatible polymer is coated with at least one silicon containing compound and wherein said biocompatible polymer has a high water binding capacity.

2. A contrast medium of claim 1 wherein the polymer is a polysaccharide.

3. A contrast medium of claim 2 wherein the polysaccharide is selected from the group consisting of arabinans, fructans, fucans, galactans, galacturonans, glucans, mannans, xylans, levan, fucoidan, carrageenan, galactocarolose, pectic acid, amylose, pullulan, glycogen, amylopectin, cellulose, carboxymethylcellulose, hydroxymethyl cellulose, hydroxypropyl methylcellulose, methyl cellulose, methoxycellulose, dextran, pustulan, chitin, agarose, keratan, chondroitin, dermatan, hyaluronic acid, alginic acid, xanthan gum, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, mannuronic acid, glucosamine, galactosamine, and neuraminic acid.

4. A contrast medium of claim 1 wherein the polymer is cellulose or a modified cellulose polymer.

5. A contrast medium of claim 1 wherein the anti-gas agent is selected from the group consisting of activated charcoal, aluminum carbonate, aluminum hydroxide, aluminum phosphate, calcium carbonate, dihydroxyaluminum sodium carbonate, magaldrate, magnesium oxide, magnesium trisilicate, sodium carbonate, loperamide hydrochloride, diphenoxylate, hydrochloride with atropine sulfate, kaolin, bismuth salts, polyoxypropylene-polyoxyethylene copolymers, polyoxyalkylene amines and imines, branched polyamines, mixed oxyalkylated alcohols, sucroglycamides, polyoxylalkylated natural oils, lauryl sulfates, 2-lactylic acid esters of unicarboxylic acids, triglyceride oils, and finely-divided polyvinyl chloride particles.

6. A contrast medium of claim 5 wherein the anti-gas agent is selected from the group consisting of activated charcoal and lauryl sulfate.

7. A contrast medium of claim 1 further comprising a suspending agent.

8. A contrast medium of claim 7 wherein the suspending agent is selected from the group consisting of xanthum gum, acacia, agar, alginic acid, aluminum monostearate, unpurified bentonite, purified bentonite, bentonite magma, carbomer 934P, carboxymethylcellulose calcium, carboxymethylcellulose sodium, carboxymethylcellulose sodium 12, carrageenan, cellulose (microcrystalline), dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, polyvinyl pyrrolidone, propylene glycol alginate, silicon dioxide, silicon dioxide colloidal, sodium alginate, and tragacanth.

9. A contrast medium of claim 1 wherein the silicon containing compound is selected from the group consisting of simethicone, protected simethicone, polysiloxane, polydimethylsiloxane, polymethylvinylsiloxane, polymethylphenolsiloxane, polydiphenylsiloxane, octamethylcyclotetrasiloxane, siloxane glycol polymer, gamma-aminopropyltriethoxysilane, diethylaminomethyltriethoxysilane, silicon dioxide, siloxyalkylene polymer, hexadimethylsilazane, hexamethyldisilazane, hexaphenylcyclotrisilazane, octamethylcyclotetrasilazane, N'N'-bis-(trimethylsilyl)acetamide, N-(dimethy(gamma-cyanopropyl)-silyl)-N-methylacetamide), and siliceous earth.

10. A contrast medium of claim 9 wherein the silicon containing compound is selected from the group consisting of simethicone.

11. A contrast medium of claim 1 wherein the polymer is in admixture with at least one silicon containing compound.

12. A contrast medium of claim 1 wherein the polymer is a natural polymer.

13. A contrast medium of claim 1 wherein the aqueous suspension is degassed.

14. A contrast medium of claim 13 wherein the contrast medium is stored under vacuum.

15. A contrast medium of claim 1 wherein the polymer comprises 0.5% by weight of an 18μ fiber length cellulose polymer; and wherein the cellulose polymer is coated with 0.25% by weight of the silicon containing compound simethicone and admixed with 500 ppm of the silicon containing compound simethicone; and further comprising an anti-gas agent comprising lauryl sulfate and a suspending agent comprising 0.3% by weight xanthan gum; and wherein the aqueous suspension is degassed and the contrast medium is stored under vacuum.

16. A contrast medium of claim 1 which is a contrast medium for use in imaging a gastrointestinal region of a patent.

17. A contrast medium of claim 1 which is a contrast medium for use in imaging a body cavity.

18. A kit for ultrasonic imaging comprising a contrast medium of claim 1.

19. A kit in accordance with claim 18 further comprising conventional ultrasonic imaging components.

20. A kit in accordance with claim 19 wherein the conventional ultrasonic imaging components are selected from the group consisting of anti-gas agents, suspending agents, flavoring materials, coloring materials, antioxidants, anticaking agents, tonicity agents, and wetting agents.

21. A contrast medium of claim 4 wherein the polymer is cellulose.

22. A contrast medium of claim 1 wherein the silicon containing compound is silicone.

* * * * *

UNITED STATES PATENT AND TRADEMARK OFFICE
CERTIFICATE OF CORRECTION

PATENT NO. : 5,714,528
DATED : Feb. 3, 1998
INVENTOR(S) : Unger et al.

It is certified that error appears in the above-identified patent and that said Letters Patent is hereby corrected as shown below:

On the title page, column 2, under "OTHER PUBLICATIONS", at "Noll et al., second line thereof, please delete "(Academin" and insert --(Academic-- therefor.

On the title page, column 2, under "ABSTRACT", last sentence thereof, please delete "maybe" and insert --may be-- therefor.

In column 3, line 45, please delete "is graph" and insert --is a graph-- therefor.

In column 6, line 19, please delete "in the an" and insert --in the art-- therefor.

In column 7, line 8, please delete "in the arc" and insert --in the art-- therefor.

In column 7, line 40, please delete "preferably" and insert --preferable-- therefor.

In column 7, line 48, please delete "ecogenicity" and insert --echogenicity-- therefor.

Signed and Sealed this

Eleventh Day of August 1998

Attest:

BRUCE LEHMAN

Attesting Officer

Commissioner of Patents and Trademarks